US011020350B2

(12) United States Patent
Peyrot et al.

(10) Patent No.: US 11,020,350 B2
(45) Date of Patent: Jun. 1, 2021

(54) PALATABLE ORAL VETERINARY COMPOSITIONS

(71) Applicant: Ceva Santé Animale, Libourne (FR)

(72) Inventors: Laurence Peyrot, La Riviere (FR); Florence Guimberteau, Montussan (FR)

(73) Assignee: Ceva Santé Animale, Libourne (FR)

( * ) Notice: Subject to any disclaimer, the term of this patent is extended or adjusted under 35 U.S.C. 154(b) by 0 days.

(21) Appl. No.: 14/404,805

(22) PCT Filed: Jun. 1, 2013

(86) PCT No.: PCT/EP2013/061332
§ 371 (c)(1),
(2) Date: Dec. 1, 2014

(87) PCT Pub. No.: WO2013/178817
PCT Pub. Date: Dec. 5, 2013

(65) Prior Publication Data
US 2015/0147393 A1    May 28, 2015

(30) Foreign Application Priority Data
Jun. 1, 2012  (FR) ........................ 1255122

(51) Int. Cl.
*A61K 31/585* (2006.01)
*A61K 9/20* (2006.01)
*A61K 9/16* (2006.01)
*A61K 31/55* (2006.01)
*A61K 9/00* (2006.01)

(52) U.S. Cl.
CPC .......... *A61K 9/2068* (2013.01); *A61K 9/0056* (2013.01); *A61K 9/1623* (2013.01); *A61K 9/1635* (2013.01); *A61K 9/1652* (2013.01); *A61K 9/2018* (2013.01); *A61K 9/2027* (2013.01); *A61K 9/2054* (2013.01); *A61K 31/55* (2013.01); *A61K 31/585* (2013.01)

(58) Field of Classification Search
None
See application file for complete search history.

(56) References Cited

U.S. PATENT DOCUMENTS

| 5,085,869 | A | * | 2/1992 | Olthoff | ................. | A61K 9/1652 424/494 |
| 6,635,278 | B1 | * | 10/2003 | Dahl | .................... | A61K 9/2009 424/451 |
| 2004/0234579 | A1 | * | 11/2004 | Finke | .................... | A61K 31/702 424/442 |
| 2009/0142401 | A1 | * | 6/2009 | Appel | ................. | A61K 9/1617 424/489 |
| 2009/0162407 | A1 | * | 6/2009 | Biggs | ..................... | A01N 25/12 424/401 |
| 2010/0062062 | A1 | | 3/2010 | McMillan et al. | | |
| 2010/0074952 | A1 | * | 3/2010 | Thoma | ................. | A61K 9/5026 424/482 |
| 2010/0183718 | A1 | * | 7/2010 | Ovaert | ................. | A61K 31/401 424/479 |

FOREIGN PATENT DOCUMENTS

| FR | 2 917 975 A1 | 1/2009 |
| JP | H11-206850 A | 8/1999 |
| WO | WO 01/87284 A2 | 11/2001 |
| WO | WO 2003/075895 A1 | 9/2003 |
| WO | WO 2007/142628 A1 | 12/2007 |
| WO | WO 2009/000843 A2 | 12/2008 |

OTHER PUBLICATIONS https://www.ulprospector.com/en/na/PersonalCare/Detail/671/28007/SYLOID-244-FP-SILICA retrieved on May 9, 2017.*
Thomason, J. D.; Rockwell, J. E.; Fallaw, T. K.; Calvert, C. A. Influence of combined angiotensin-converting enzyme inhibitors and spironolactone on serum K+, Mg2+, and Na+ concentration in small dogs with degenerative mitral valve disease. Journal of Veterinary Cardiology (2007), 9, 103-108.*
Lifelearn, Inc. Spironolactone, Medications, 2008, p. 1-4.*
https://www.sorbentsystems.com/desiccants_types.html retrieved on Mar. 12, 2018.*
Barr et al., Effects of adding spironolactone to an angiotensin-converting enzyme inhibitor in chronic congestive heart failure secondary to coronary artery disease. Am J Cardiol. Dec. 15, 1995;76(17):1259-65.
Bie et al., Enhanced atrial peptide natriuresis during angiotensin and aldosterone blockade in dogs. Am J Physiol. May 1990;258(5 Pt 2):R1101-7.
Kambara et al., Combined effects of low-dose oral spironolactone and captopril therapy in a rat model of spontaneous hypertension and heart failure. J Cardiovasc Pharmacol. Jun. 2003;41(6):830-7.
VICH GL3 (Stability 1) Stability Testing of New Veterinary Drug Substances and Medicinal Products. VICH Committee. May 20, 1999. 11 pages.
Yoshioka, S. Effect of Moisture on Stability of Solid Dosage Forms. Pharm. Tech. Japan, vol. 6, No. 8, pp. 891-905, 1990.
U.S. Appl. No. 16/776,324, filed Jan. 29, 2020, Peyrot et al.
[No Author Listed] 2.5.12 Water: Semi-micro determination. European Pharmacopoeia. Apr. 2018:1 page.

(Continued)

*Primary Examiner* — Jessica Worsham

(74) *Attorney, Agent, or Firm* — Wolf, Greenfield & Sacks, P.C.

(57) ABSTRACT

The present invention concerns palatable veterinary compositions made from one or more pharmaceutical active ingredients having a smell and/or a taste that is repulsive to animals, and a preparation method for preparing said oral veterinary compositions.

6 Claims, 1 Drawing Sheet

(56) References Cited

OTHER PUBLICATIONS

[No Author Listed] 2.5.32 Water: Micro determination. European Pharmacopoeia. Jul. 2019:1 page.
[No Author Listed] Test procedures and acceptance criteria for new veterinary drug substances and new medicinal products: chemical substances. VICH GL39. Nov. 2005:1-35.
Padivitage et al., Water determination. Specification of Drug Substances and Products Jan. 1, 2014;223-41.

* cited by examiner

PALATABLE ORAL VETERINARY COMPOSITIONS

RELATED APPLICATIONS

This application is a national stage filing under 35 U.S.C. § 371 of international application PCT/EP2013/061332, filed Jun. 1, 2013, entitled "Palatable oral veterinary compositions," which claims priority to French Application Serial No. 1255122, filed on Jun. 1, 2012, each of which is herein incorporated by reference in its entirety.

The subject of the present invention is palatable oral veterinary compositions based on one or more pharmaceutical active substances having an odor and/or taste repulsive to animals, and a process for preparation for preparation of said oral veterinary compositions.

Administration of pharmaceutical active substances whose taste and/or odor are repulsive is always a problem in the case of animals, and generally requires the addition of a palatabilizing agent in order to mask the bad taste or the unpleasant odor of these pharmaceutical active substances and thus to thwart the animals' highly developed sense of smell.

The palatabilizing agents used are generally aromas, yeasts, proteins, protein hydrolyzates, gelatin, etc., and are most commonly hygroscopic products with a high free residual water greater than 3%. Major problems of incompatibility and instability thus arise if these are to be formulated with pharmaceutical active substances sensitive to moisture.

To solve this problem, those skilled in the art have inclined towards physical separation of the pharmaceutical active substance and the palatabilizing agent for example by coating the active substance or substances with a protective film. Further, this coating makes it possible to mask the taste of the pharmaceutical active substance thus limiting the quantities of palatabilizing agent to be incorporated. This strategy necessitates the inclusion of an additional stage in the production process and an associated additional cost.

The Applicants have discovered that it sufficed to obtain a free residual water level less than a limit of 1.5% in order to overcome the problems of incompatibility between said "moist" or hygroscopic palatabilizing agent and the pharmaceutical active substance, and thus to obtain optimal stability after formulation of the latter.

SUMMARY OF INVENTION

The subject of the present invention is thus a process for preparation of a palatable oral veterinary composition, comprising a stage of mixing one or more pharmaceutical active substances having an odor and/or a taste repulsive to animals with at least one palatabilizing agent, and a stage of after-drying of the mixture in order to obtain a quantity of free residual water in the after-dried mixture of between 0 and 1.5% by weight.

The content of free residual water is preferably determined by the Karl Fisher titration process after deducting the quantity of any bound water (or water of crystallization) in the ingredients of the composition:

Free residual water=Karl Fisher total water−bound water

The present invention also relates to a palatable oral veterinary composition comprising at least one pharmaceutical active substance having an odor and/or a taste repulsive to animals and at least one palatabilizing agent, the percentage of free residual water in said veterinary composition being between 0 and 1.5% by weight.

DETAILED DESCRIPTION OF THE INVENTION

Figure 1:
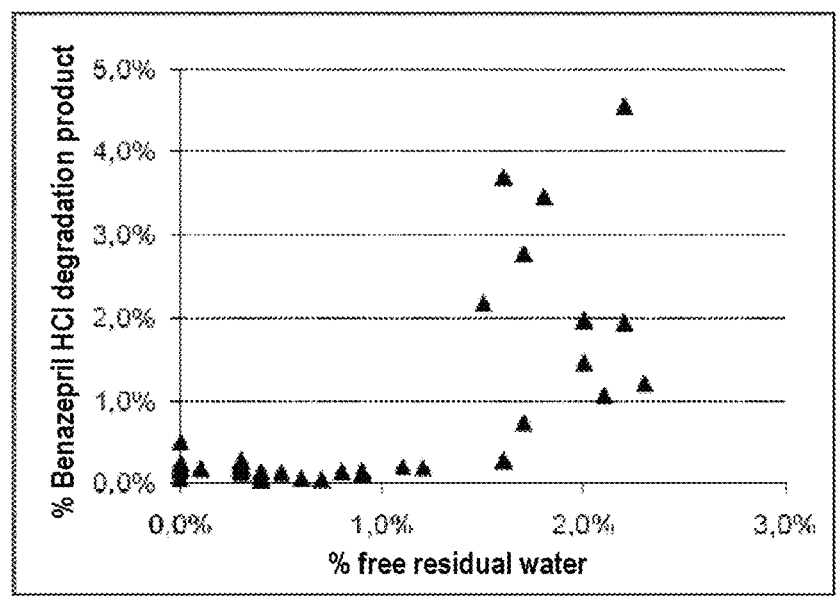
FIG. 1: is a graph showing the effect of the free residual water on the quantity of degradation products generated during storage of a benazepril HCl composition.
Figure 2:
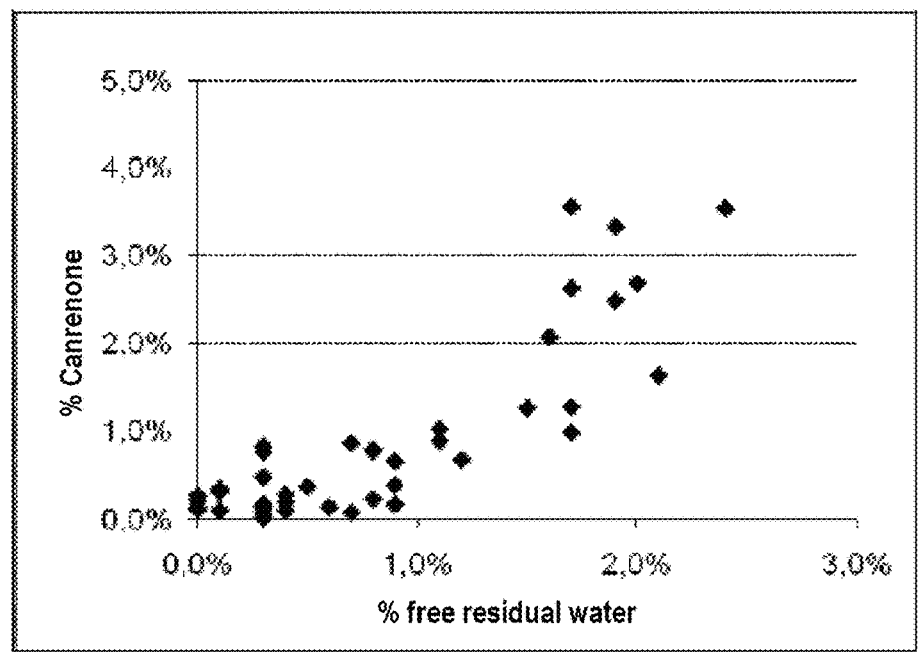
FIG. 2: is a graph showing the effect of the free residual water on the quantity of degradation products (canrenone) generated during storage of a spironolactone composition.

The present invention thus relates to a process for preparation of a palatable oral veterinary composition comprising (i) a stage of mixing one or more pharmaceutical active substances having an odor and/or a taste repulsive to animals with at least one palatabilizing agent, and (ii) a stage of after-drying of the mixture such that the quantity of free residual water in the mixture after the post-drying stage is between 0 and 1.5% by weight, relative to the total weight of the composition.

The free residual water is preferably determined by the Karl Fisher titration, deducting the quantity of any bound water present in the composition.

The present invention is in fact based on the discovery of the existence of a critical value for the free residual water of the oral veterinary composition below which the problems of incompatibility between the hygroscopic palatabilizing agent and the pharmaceutical active substance and of instability of the latter are solved. More specifically, the pharmaceutical active substance remains stable after formulation with the palatabilizing agent when the free residual water obtained after drying was less than 1.5%.

The Karl Fisher titration method is an efficient, rapid and reliable method intended for determination of the quantity of water in a great variety of samples or pharmaceutical active substances and over a wide concentration range. It is based on the reaction of oxidation of sulfur dioxide by iodine dissolved in methanol and a base such as pyridine, according to the following reaction:

$$SO_2 + I_2 + H_2O \rightarrow H_2SO_4 + HI \text{ at pH between 5 and 7}$$

In this reaction, the sulfuric acid $SO_2$ and hydriodic acid $I_2$ only react in presence of water. The iodine taking part in the reaction is generated directly in the titration cell by an electrochemical oxidation of iodide until unreactive iodine is detected. The end point is determined by colorimetry or amperometry. This method is in particular used to check compliance during the production of lyophilized medicaments.

There are many devices on the market for facilitating this estimation. As examples, the Karl Fischer volumetric titrator TIM550® marketed by Radiometer Analytical, the Titrino KF®, the Titrando KF® or the Coulometer KF® may be mentioned.

The bound water or water of crystallization can be determined experimentally for example by means of thermogravimetric analysis (direct measurement of changes in mass as a function of the temperature). Thus, the free water is eliminated at temperatures below about 100° C. while the bound water is only eliminated at temperatures above 100° C. The bound water or water of crystallization can also be determined theoretically when the degree of hydration of a molecule is known.

According to the process of the present invention, the free residual water content of the hygroscopic palatabilizing agent can be greater than 1.5% by weight relative to the total weight of the composition.

The process according to the present invention is particularly useful for the formulation of palatable oral veterinary compositions comprising one or more pharmaceutical active substances having a repulsive odor and/or taste. These are for example aldosterone antagonists, angiotensin conversion enzyme inhibitors, antagonists of the AT-1 receptor of angiotensin II, inotropic agents, inodilators, vasodilators, diuretics, digitalis drugs, beta blockers and/or calcium antagonists. The process is also advantageous when said pharmaceutical active substances are unstable and sensitive to moisture.

Among the aldosterone antagonists, spironolactone and eplerenone, or the metabolites of these compounds, which among others include canrenone, canrenoic acid, 1513-OH canrenone, 21-OH canrenone, potassium canrenone, 7α-thio-spironolactone, 7α-thiomethyl-spironolactone or 6-β-hydroxy-7-α-thiomethyl spironolactone may be mentioned.

Among the angiotensin conversion enzyme inhibitors, alacepril, benazepril, captopril, cilazapril, delapril, enalapril, fosinopril, imidapril, idrapril, lisinopril, perindopril, quinapril, ramipril, saralasin acetate, termocapril, trandolapril, ceranapril, moexipril, spirapril and their pharmaceutically acceptable derivatives of these compounds such as in particular the salts and esters may be mentioned.

Among the inodilators, pimobendane or levosimendane may be mentioned.

The pharmaceutical active substances are preferably spironolactone and/or benazepril and/or enalapril.

These compositions are particularly useful for treating non-human animals suffering from cardiac insufficiency such as congenital cardiopathy or acquired cardiopathy as described in particular in the international publication WO 2009/000843. Also a subject of the present invention is the veterinary compositions as previously described, for use thereof in the treatment and/or the prevention of cardiac insufficiency in non-human animals.

The veterinary compositions according to the present invention can thus for example comprise therapeutically effective daily doses of an aldosterone receptor antagonist such as spironolactone and/or derivatives or metabolites thereof of between about 0.88 and 5 mg/kg/day (preferably about 2 mg/kg/day) and doses of angiotensin conversion enzyme inhibitors, such as benazepril, of between 0.1 to 0.6 mg/kg/day (preferably about 0.25 mg/kg/day).

Other active substances are for example compounds having antiparasitic activity against endoparasites and/or ectoparasites. These for example include the macrocyclic lactones: avermectins and milbemycins such as preferably ivermectin, eprinomectin, selamectin, moxidectin and milbemycin oxime, benzimidazoles, imidazothiazoles, tetrahydropyrimidines, organophosphates, piperazines, antimicrobial agents or also antibiotic agents such as preferably amoxicillin.

Other pharmaceutical active substances may be selected from organosulfur compounds such as omeprazole, aiming to reduce the acid secretions of the stomach.

Palatabilizing agents which can be used in the process according to the present invention are also well known in the field. These are for example aromas, yeasts, proteins, protein hydrolyzates, gelatin, starch or pre-gelatinized starch, phosphoric acid-based compounds, disodium pyrophosphate, tetrasodium pyrophosphate, etc.

The after-drying stage can be effected by all means well known in the field, for example by placing the composition under partial vacuum to accelerate the drying or else by addition of a desiccating or drying agent such as for example silica gel, drying agents of the anhydrous calcium chloride type, molecular sieves, drying tunnels, microwave drying systems, etc.

Preferably, the compositions are produced and/or packed under reduced humidity.

According to the process of the invention, the free residual water content after the drying stage is preferably maintained between 0 and 1.5% by weight relative to the total weight of the composition.

This residual water content is preferably determined by the Karl Fisher titration from which the quantity of bound water possibly present in the ingredients of the composition is deducted.

The oral veterinary compositions obtained by the process described above have superior palatability properties, and these are preferably better than 50% spontaneous intake.

Said oral veterinary compositions can be in all forms appropriate for administration by the oral route. They can thus for example be in solid or semi-solid form, powders, tablets, capsules, granules, coated tablets, gel capsules, sprays, cachets, pills, lozenges or pastes.

The oral veterinary compositions obtained by the process described above also have better stability on storage. They are in fact stable for at least 24 months without any special storage condition in the sense of the recommendations published on May 20, 1999 by the VICH committee under the title VICH GL3 (Stability 1) "Stability Testing of New Veterinary Drug Substances and Medicinal Products". In fact, as was demonstrated in the examples below, less than 3% is degraded after 24 months of storage at temperatures of 25-30° C. and at 60-65% relative humidity (RH).

According to a second aspect, a subject of the present invention is palatable oral veterinary compositions comprising one or more pharmaceutical active substances having an odor and/or a taste repulsive to animals, at least one hygroscopic palatabilizing agent, and possibly excipients possibly having a percentage of free residual water greater than 1.5%. Preferably, the content of free residual water in the veterinary compositions is between 0 and 1.5% by weight.

The pharmaceutical active substances and the palatabilizing agents are as previously described.

The oral veterinary compositions according to this aspect of the present invention are particularly advantageous since they make it possible to obtain a palatability greater than 50% spontaneous intake in a simple manner. They also exhibit stability characteristics on long-term storage which are superior to the compositions whose free residual water is greater than 1.5%.

Likewise, the compositions according to the invention can comprise any other pharmaceutically acceptable excipient, such as sugars (lactose, lactose monohydrate, saccharose, dextrose, glucose, etc.), cellulose or starches, a disintegrating agent, lubricants, binders, diluents, antioxidants, flow agents, complexing agents, preservatives, colorants, or buffering agents, etc.

As the lubricant, stearic acid, magnesium stearate, colloidal silica or, for example, glycerol tribehenate can be used. As the disintegrating agent, croscarmellose, crospovidone or starch derivatives can be used. Examples of binders include methylcellulose, hydroxyethyl-cellulose, xanthan gum, povidone, microcrystalline cellulose, etc.

EXAMPLES

Example 1: Preparation of Palatable Veterinary Compositions of Spironolactone Tablets of spironolactone were prepared according to a process with two main stages: wet granulation followed by tableting.

Stage 1: Granulation

During the granulation stage, the ingredients listed in table 1 below were mixed dry, granulated with water in a DIOSNA high shear granulator, then dried in the oven.

TABLE 1

| Granulation ingredients | Composition in % (m/m) |
|---|---|
| Spironolactone | 20 |
| Lactose monohydrate | 40 |
| Microcrystalline cellulose | 25 |
| Crospovidone | 5 |
| Povidone | 10 |

Stage 2: Tableting

The granules obtained at the end of stage 1 were next mixed with tableting excipients and the palatabilizing agents then tableted by means of a FROGERAIS press. The final composition of the 250 mg tablets is given in table 2 below.

TABLE 2

| Tableting ingredients | Composition in % (m/m) |
|---|---|
| Spironolactone granules | 60 |
| Artificial pig liver aroma | 15 |
| Compressible sugar | 20 |
| Crospovidone | 4 |
| Magnesium stearate | 1 |

Example 2: Preparation of Palatable Veterinary Compositions of Benazepril

Tablets of benazepril HCl were prepared according to a process with two main stages: wet granulation followed by tableting.

Stage 1: Granulation

During the granulation stage, the ingredients listed in table 3 below were mixed dry, granulated with ethanol in a DIOSNA high shear granulator, then dried under vacuum.

TABLE 3

| Granulation ingredients | Composition in % (m/m) |
|---|---|
| Benazepril HCl | 2 |
| Lactose monohydrate | 60 |
| Microcrystalline cellulose | 30 |
| Crospovidone | 3 |
| Povidone | 5 |

Stage 2: Tableting

The granules obtained at the end of stage 1 were next mixed with tableting excipients and the palatabilizing agents then tableted by means of a FROGERAIS press. The final composition of the 200 mg tablets is given in table 4 below.

TABLE 4

| Tableting ingredients | Composition in % (m/m) |
|---|---|
| Benazepril HCl granules | 50 |
| Artificial chicken aroma | 20 |
| Compressible sugar | 25 |
| Crospovidone | 4 |
| Magnesium stearate | 1 |

Lactose monohydrate contains 5% bound water. The tablets of example 2 thus contain 1.5% of bound water contributed by the lactose monohydrate.

Example 3: Preparation of Palatable Veterinary Compositions of Spironolactone and Benazepril HCl Combination tablets simultaneously containing spironolactone and benazepril HCl were prepared according to a two stage process.

The composition of the combination tablets is given in table 5 below:

TABLE 5

| Ingredient | Composition in % (m/m) |
|---|---|
| Spironolactone and benazepril HCl granules | 66.2 |
| Artificial beef aroma | 20.0 |
| Compressible sugar | 10.0 |
| Crospovidone | 3.0 |
| Magnesium stearate | 0.8 |

Example 4: Stability and Free Residual Humidity Tests

The tablets from example 3 were placed in high density polyethylene (HDPE) pillboxes and stored in climatic enclosures at 25° C./60% RH and 30° C./65% RH. Analyses were performed regularly for 2 years. The results are given in table 6 below.

TABLE 6

| Storage | Test | Stability point | | | | | | |
|---|---|---|---|---|---|---|---|---|
| | | 0 | 3 mth | 6 mth | 9 mth | 12 mth | 18 mth | 24 mth |
| Storage condition 25° C./60% RH | free residual water content (%) | 0.2 | 0.0 | 0.2 | 0.3 | 0.2 | 0.5 | 0.6 |
| | Spironolactone dosage (mg/tablet) | 40.3 | 40.2 | 39.8 | 39.4 | 39.9 | 39.8 | 39.9 |

TABLE 6-continued

| Storage | Test | 0 | 3 mth | 6 mth | 9 mth | 12 mth | 18 mth | 24 mth |
|---|---|---|---|---|---|---|---|---|
| | spironolactone degradation product (%) | 0.2 | 0.3 | 0.4 | 0.5 | 0.5 | 0.7 | 0.9 |
| | benazepril HCl dosage (mg/tablet) | 5.05 | 5.01 | 5.02 | 4.95 | 4.96 | 4.92 | 4.99 |
| | benazepril HCl degradation products (%) | <LOQ | 0.2 | 0.4 | 0.4 | 0.4 | 0.7 | 0.7 |
| Storage condition 30° C./65% RH | free residual water content (%) | 0.2 | 0.2 | 0.2 | 0.5 | 0.4 | 0.3 | 1.0 |
| | spironolactone dosage (mg/tablet) | 40.3 | 40 | 39.7 | 39 | 39.9 | 39.8 | 39.7 |
| | spironolactone degradation product (%) | 0.2 | 0.4 | 0.5 | 0.7 | 0.8 | 1.3 | 1.6 |
| | benazepril HCl dosage (mg/tablet) | 5.05 | 4.99 | 5.01 | 4.89 | 4.96 | 4.91 | 4.95 |
| | benazepril HCl degradation products (%) | <LOQ | 0.3 | 0.4 | 0.5 | 0.5 | 0.9 | 1.1 |

The total impurity contents remain at very low levels (<3%) after 2 years' storage when the free moisture in the tablets remains low.

Example 5: Comparative Example

Tablets of composition identical to that of example 3 were stored at 25° C./60% RH in such a manner as to have tablets with free residual water contents which were high (comparative example) or low according to the present inventions.

The analyses at 3 and 6 months showed that the development of degradation products was high when the free residual water content is greater than the threshold of 1.5%. In the long term, the tablets having a high free residual moisture level were not sufficiently stable.

TABLE 7

| Product | Test | 3 months | 6 months |
|---|---|---|---|
| Comparative example | free residual water content (%) | 2.1 | 2.5 |
| | spironolactone degradation product (%) | 0.6 | 1.1 |
| Invention | free residual water content (%) | 0.6 | 0.3 |
| | spironolactone degradation product (%) | 0.1 | 0.2 |

The invention claimed is:

1. A process for preparation of a palatable oral veterinary composition, comprising the following steps:
   a stage of granulating a mixture comprising spironolactone having an odor and/or a taste repulsive to animals in the presence of water to obtain granules of spironolactone;
   a stage of drying the granules of spironolactone; and
   a stage of tableting comprising mixing the dried granules of spironolactone with a hygroscopic palatabilizing agent and tableting the obtained mixture to obtain tablets, wherein the concentration of said hygroscopic palatabilizing agent is between 15% and 20% (m/m), wherein the composition of said tablets has a free residual water content between 0 and 1.5% by weight, relative to the total weight of the composition, as determined by the Karl Fischer titration method, and wherein less than 3% of spironolactone is degraded after 24 months of storage at temperatures of 25-30° C. and at 60-65% relative humidity.

2. The process of claim 1, wherein the stage of tableting further comprises mixing the dried granules of spironolactone with at least one excipient and/or at least one lubricant.

3. The process of claim 1, wherein the palatability of the composition is greater than 50% spontaneous intake.

4. The process of claim 1, wherein the drying stage is effected by addition of a desiccating agent or a drying agent.

5. The process of claim 4, wherein the desiccating agent or drying agent is silica gel.

6. The process of claim 1, wherein the mixture comprising spironolactone in the stage of granulating further comprises benazepril.

* * * * *